United States Patent [19]

Termanini

[11] 4,237,875
[45] Dec. 9, 1980

[54] DYNAMIC INTRAMEDULLARY COMPRESSION NAILING

[75] Inventor: Zafer Termanini, 506 New Rochelle Rd., Bronxville, N.Y. 10708

[73] Assignee: Towmotor Corporation, Mentor, Ohio

[21] Appl. No.: 14,558

[22] Filed: Feb. 23, 1979

[51] Int. Cl.³ .............................................. A61F 5/04
[52] U.S. Cl. ................................................ 128/92 BA
[58] Field of Search ............ 128/92 BC, 92 B, 92 BB, 128/92 BA, 92 R, 92 EB, 92 EC, 83 R; 32/10 A

[56] References Cited

U.S. PATENT DOCUMENTS

| 624,969 | 0/1899 | Petterson | 128/92 B |
| 1,091,674 | 0/1914 | Lee | 128/92 BB |
| 2,077,804 | 0/1937 | Morrison | 128/92 BA |
| 2,485,531 | 0/1949 | Dzus et al. | 128/92 B |
| 2,685,877 | 0/1954 | Dobelle | 128/92 CA |
| 3,738,008 | 0/1973 | Edelman | 32/10 A |
| 3,986,504 | 0/1976 | Avila | 128/92 BC |

FOREIGN PATENT DOCUMENTS

| 1075793 | of 1960 | Fed. Rep. of Germany | 32/10 A |
| 2246274 | of 1974 | Fed. Rep. of Germany | 128/92 BC |
| 2811939 | of 1978 | Fed. Rep. of Germany | 32/10 A |
| 161547 | of 1957 | Sweden | 128/92 BC |
| 453570 | of 1968 | Switzerland | 128/92 BC |
| 487638 | of 1976 | U.S.S.R. | 128/92 BC |

Primary Examiner—Robert W. Michell
Assistant Examiner—C. W. Shedd
Attorney, Agent, or Firm—Kenyon & Kenyon, Reilly, Carr & Chapin

[57] ABSTRACT

A dynamic compression nail for intramedullary compression nailing in treating the fractures of long bones includes a proximal part having at its distal end a central cylindrical recess open on the distal end and a central bore through the remaining portion of the part; a distal part having a tip portion and a portion attached thereto for insertion into said cylindrical cavity, the distal part also containing a central bore; a central axial compression shaft extending through the bores in the proximal and distal parts; a spring surrounding the shaft and acting between the proximal end of the cylindrical recess and the distal part biasing the distal part distally; at least one pair of sliding blades having on the side thereof pointed projections in each of the said proximal and distal parts, the sliding blades operatively coupled to the shaft by means of pins so that retraction of the shaft proximally will result in an outward projecting movement of the said sliding blades thereby permitting their projecting spikes to engage the bone; and means for moving said shaft.

12 Claims, 14 Drawing Figures

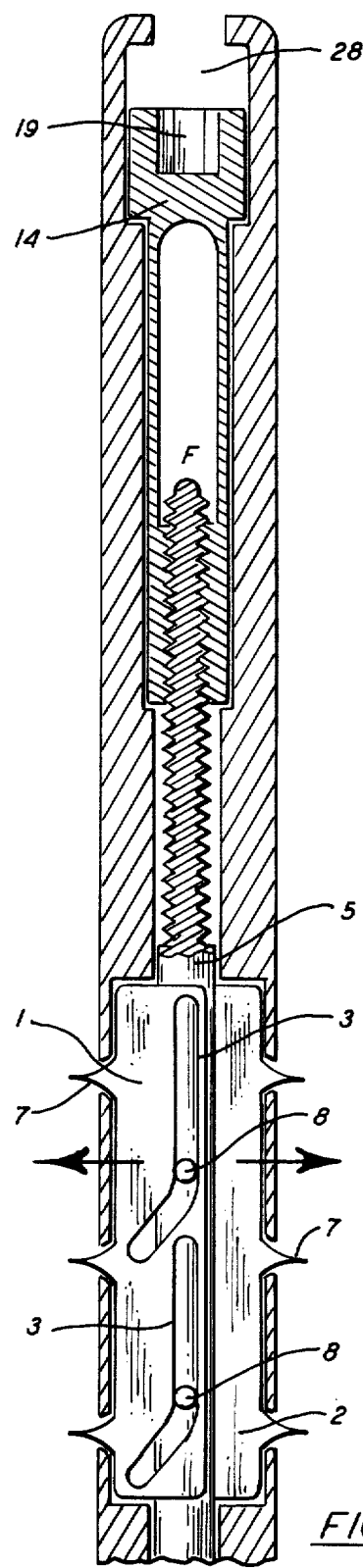
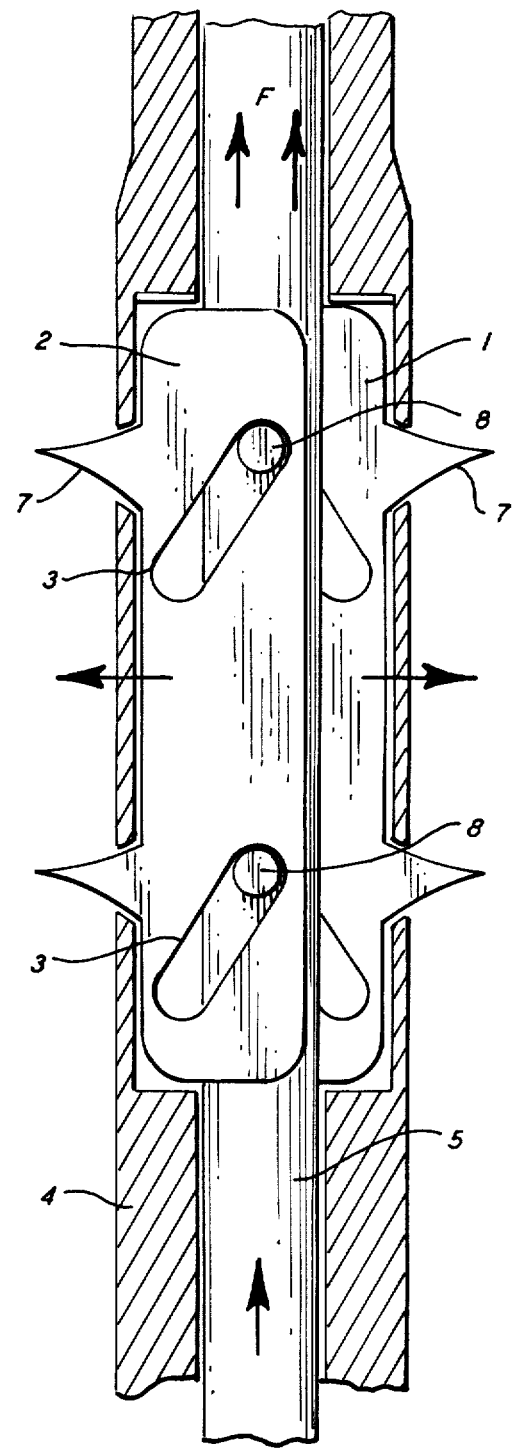
FIG. 3
FIG. 4

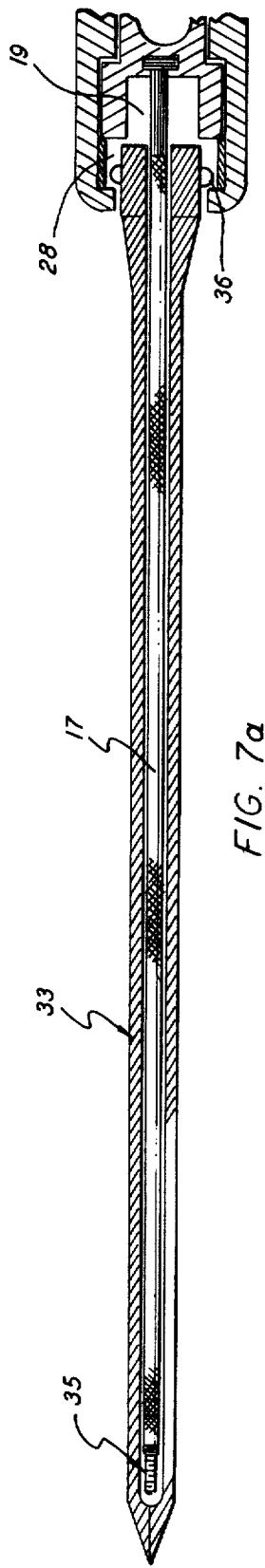
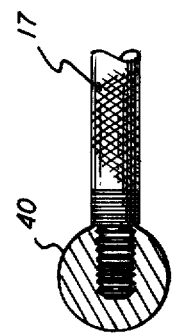
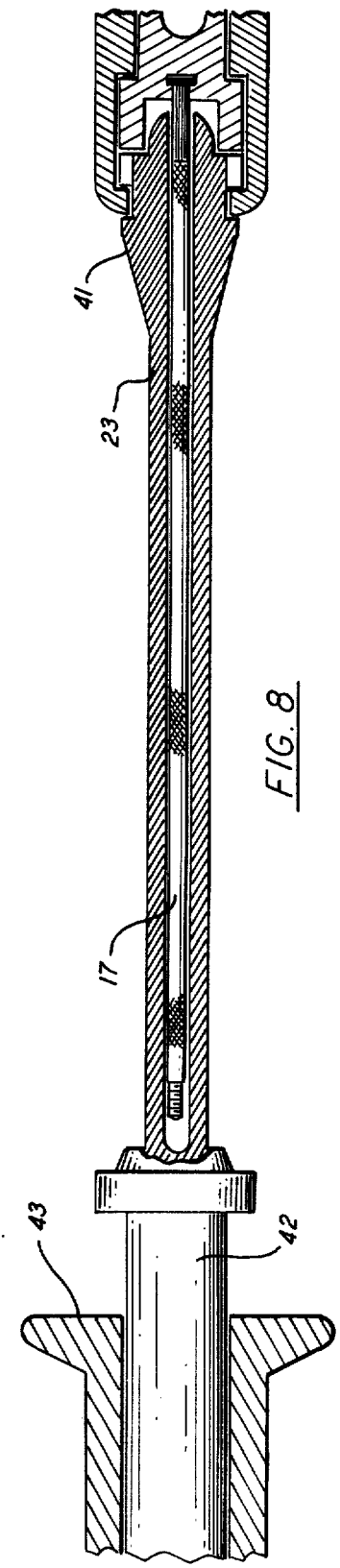

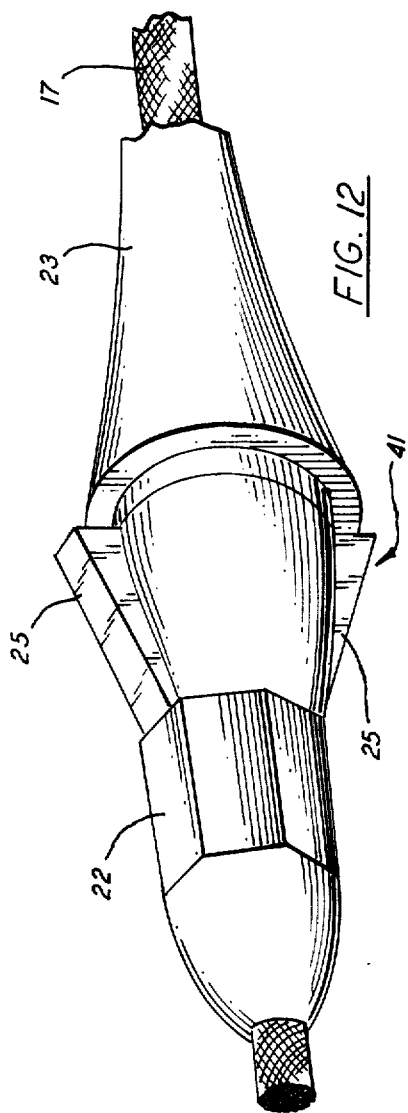
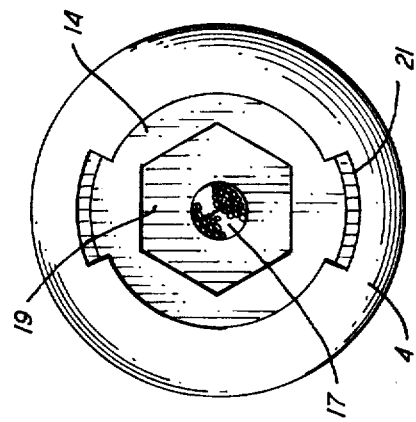
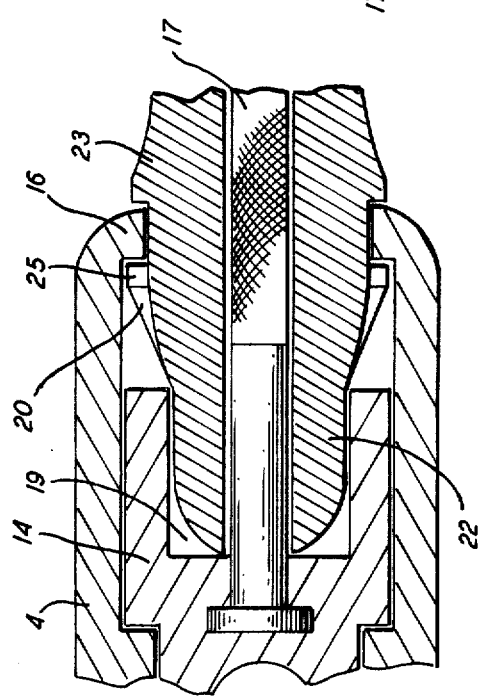
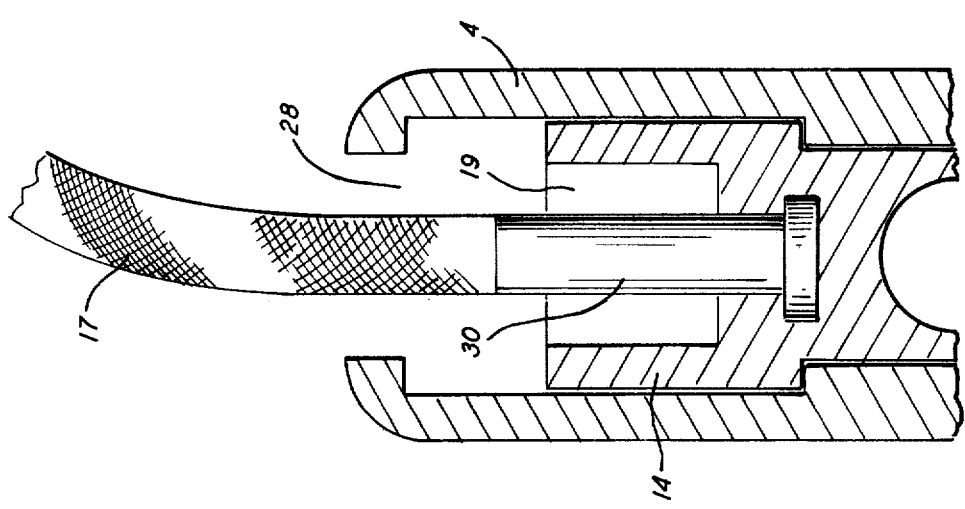

DYNAMIC INTRAMEDULLARY COMPRESSION NAILING

BACKGROUND OF THE INVENTION

This invention relates to the treating of fractures of long bones in general and more particularly to an improved intramedullary nail and a method of using such a nail.

Albin Lambotte of Belgium is given credit for using the first intramedullary nail in a clavicle in 1907, as cited by C. Wier in the American Journal of Orthopedic Surgery, Vol. 12, No. 2, Feb., 1970. Rissler in 1911, as indicated by Kuntschner in Practice of Intramedullary Nailing, Springfield, Ill., 1970, Charles C. Thomas, Publisher, and Schoene in 1913, as described in the book Zur Behundlung Von Vondrarmfracturen mit Bolzung Muhch, performed some earlier attempts, but the method and the materials were either inadequate or of poor quality for stable fixation and generally required additional external means for immobilization. Hey Grove of England as described in his book, On Modern Methods of Treating Fractures., Bristol, 1916, John Wright & Son Ltd., was the first to use a long intramedullary hollow tube and a rod (cross shaped in section) in femurs. Rush, treated and published the first case on an intramedullary nail in the U.S. for fractures in 1937 (Rush L. V. and Rush H. L., A Technique For Longitudinal Pin Fixation of Certain Fractures Of The Ulna And the Femur). In W.W.II, German Air Forces needed men desperately during the later stages of the War. Kuntschner, as described in Die Technik Der Marknagelung Des Oberschenkels, Zentralb. Chir., extensively used the intramedullary nailing to treat fractures of femur and sent German pilots back into action a few days after injury without any external support and without apparent pain.

Additional information concerning intramedullary nailing is contained in an article by K. Clawson, entitled Closed Intramedullary Nailing of the Femur.

Although, intramedullary nails and techniques of using these have been in use for a number of years as evidenced from the above, the devices presently in use are sometimes difficult to work with and not completely satisfactory. There thus exists a need for better intramedullary nails and improved manner of using such a nail.

SUMMARY OF THE INVENTION

The present invention provides an improved intramedullary nail in the form of a dynamic compression nail which includes a proximal part with lateral projections retractable into the body of the dynamic compression nail, which are variable in number and size; a distal tip with retractable lateral projections, an axial compression shaft which is retracted proximally by a retracting head located in the proximal part and an extraction cable located at the proximal tip of the dynamic compression nail and used to facilitate extraction thereof without surgical exposer of greater trochanter. In the dynamic compression nail of the present invention, a spring load of appropriate strength and resistance synchronizes, in terms of time, the projection of the lateral spikes, or projections, when an inserter driver is turned so as to carry out the following sequence:

(A) The distal and proximal spikes are extended; and then (B) Compression takes place.

In addition to the classical advantages offered by the commonly used intramedullary nails, the device of the present invention offers the following advantages:

Compression of the bone fragments at the fracture site by the application of retracting screw mechanism is obtained. This would be indicated and helpful in treatment of severely comminuted fractures, old ununited shaft fractures and other conditions where compression of the bone fragment is indicated.

Stability of the bone fragments: The solid grip on the inner surface of the intramedullary canal supplied by the lateral projections located proximal and distal to the fracture site eliminate the problem of rotation of the fragments and offers solid stability required for rapid healing of the fracture.

Means for simple extraction of the nail: A flexible and tension resistant cable is firmly attached to the proximal end of the nail. At the end of the insertion procedure, the cable is curled and buried under the skin in the subcutaneous tissue. When the fracture is healed, and bone continuity is restored, the nail can be removed by exposing the tip of the flexible cable which will be used as a guide wire to guide the tip of the extractor, down to the proximal tip of the dynamic compression nail. The tip will be lodged in the extraction recesses and traction can be applied to remove the nail.

It is also possible to remove the nail in simpler fashion by making a simple skin incision to expose the tip of the flexible cable, and then apply, to the tip, an extractor. Such is particularly useful in cases where the proximal tip of the dynamic compression nail is covered by overgrowing bone.

Also disclosed are various methods of utilizing the dynamic compression nail of the present invention including open nailing, closed nailing using mobil X-ray image intensifier and television equipment, and semi-closed nailing.

BRIEF DESCRIPTION OF THE DRAWINGS

FIG. 3 is a cross-sectional view illustrating operation of the proximal spikes.

FIG. 4 is a detail illustrating the manner in which the projecting spikes are extended at the distal end.

FIG. 7a is a detail of a protective sheath used with the nail of the present invention.

FIGS. 7b and 7c are details of optional tips for the flexible cable used with the nail of the present invention.

FIG. 8 is a cross-sectional view showing the retraction and insertion tool in place in the proximal end of the nail.

FIG. 11 is an illustration in cross-section of the proximal end showing attachment of the cable.

FIG. 12 is a perspective view of the retracting head.

FIG. 13 is a top view of the proximal tip illustrating the hexagonal recess of the retracting head.

FIG. 14 is a cross-section of the proximal tip showing the tip of the inserter driver in place.

DETAILED DESCRIPTION OF THE INVENTION

Figures 1, 2:
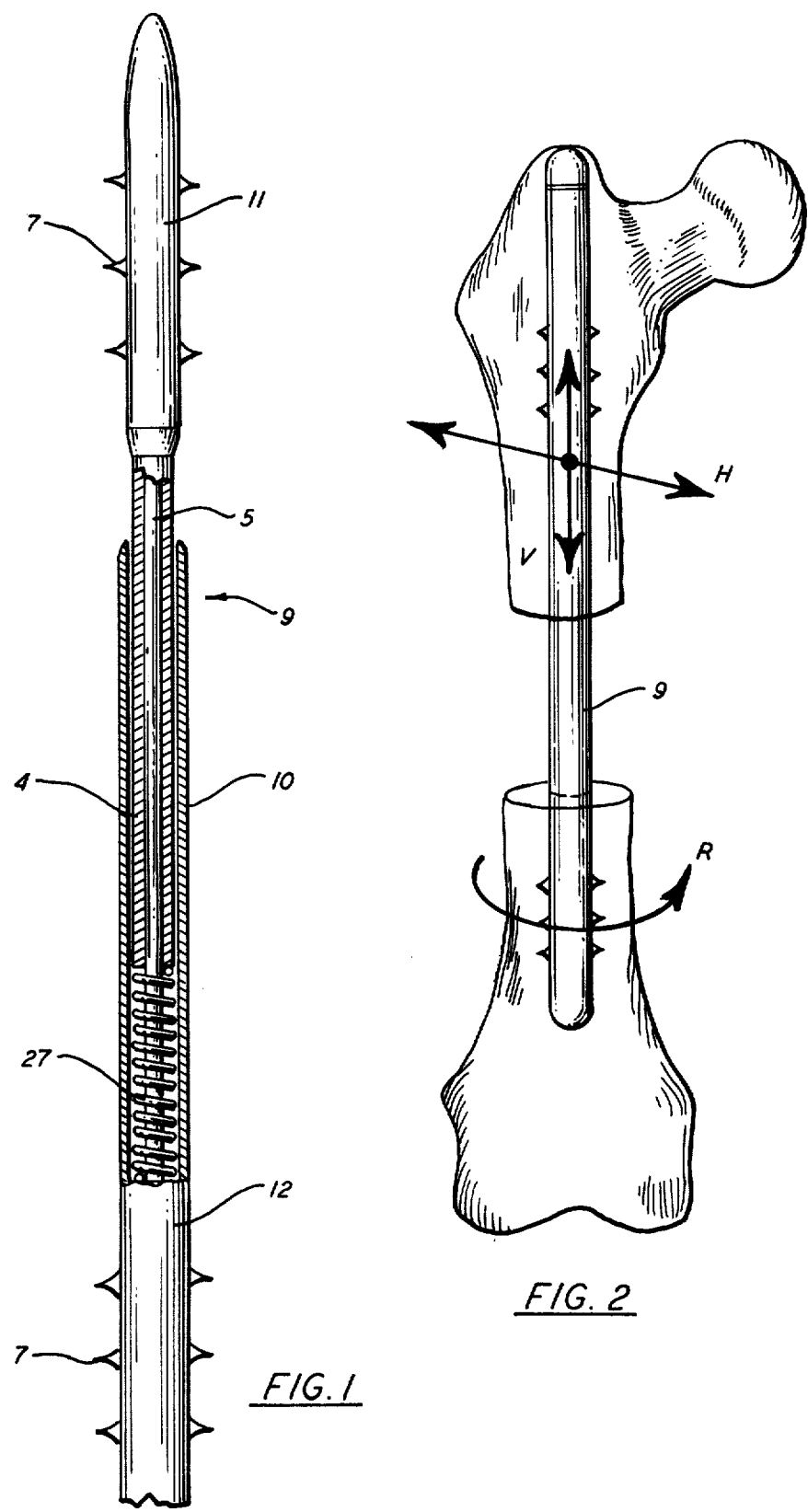
FIG. 1 is a longitudinal view, partially in cross-section, of the dynamic compression nail of the present invention.
FIG. 2 is an illustration of the nail of the present invention in place, demonstrating the rotation and axial stability offered thereby.

FIG. 1 is a view, partially in cross-section, of the dynamic compression nail 9 of the present invention. The dynamic compression nail includes a proximal part 12 with lateral projections 7 which may be variable in number and size in a manner to be more fully explained below. The lateral projections are retractable into the body of the dynamic compression nail. It also includes a distal tip 11 with similar retractable lateral projections 7. Extending to a point within the distal tip is an axial compression shaft which can be retracted proximally by a retracting head, not shown in the figure, located in the proximal part 12. This will be explained in more detail below. An extraction cable is located at the proximal tip of the nail and used to facilitate extraction without surgical exposure of the greater trochanter. A spring load 27 of appropriate strength and resistance is disposed within an appropriate recess in the proximal part 12 and is used to synchronize, in terms of time, the projection of the lateral spikes 7 when the inserter driver is turned. In a manner to be more fully explained below, the sequence of operation is that the distal spikes are extended, the proximal spikes extended, and then compression takes place.

As is evident from the illustration of FIG. 2, when the nail 9 of the present invention is in place it provides stability in the rotational, R, horizontal, H, and vertical, V, directions.

The mechanism by which the nail of the present invention carries out its function can best be seen through referenced FIGS. 1, 3, 4 and 5. Referring to FIG. 3, the axial compression shaft 5, is shown in a cross-section through the proximal end. Shaft 5 contains a thread on its end and is engaged by a retracting screw head 14 having a hexagonal recess 19 for accepting an Allen-type wrench. During the insertion, a proper tool is inserted in the recess 19 and rotation carried out. This results in the shaft 5 being drawn toward the proximal end.

Figures 9, 10:
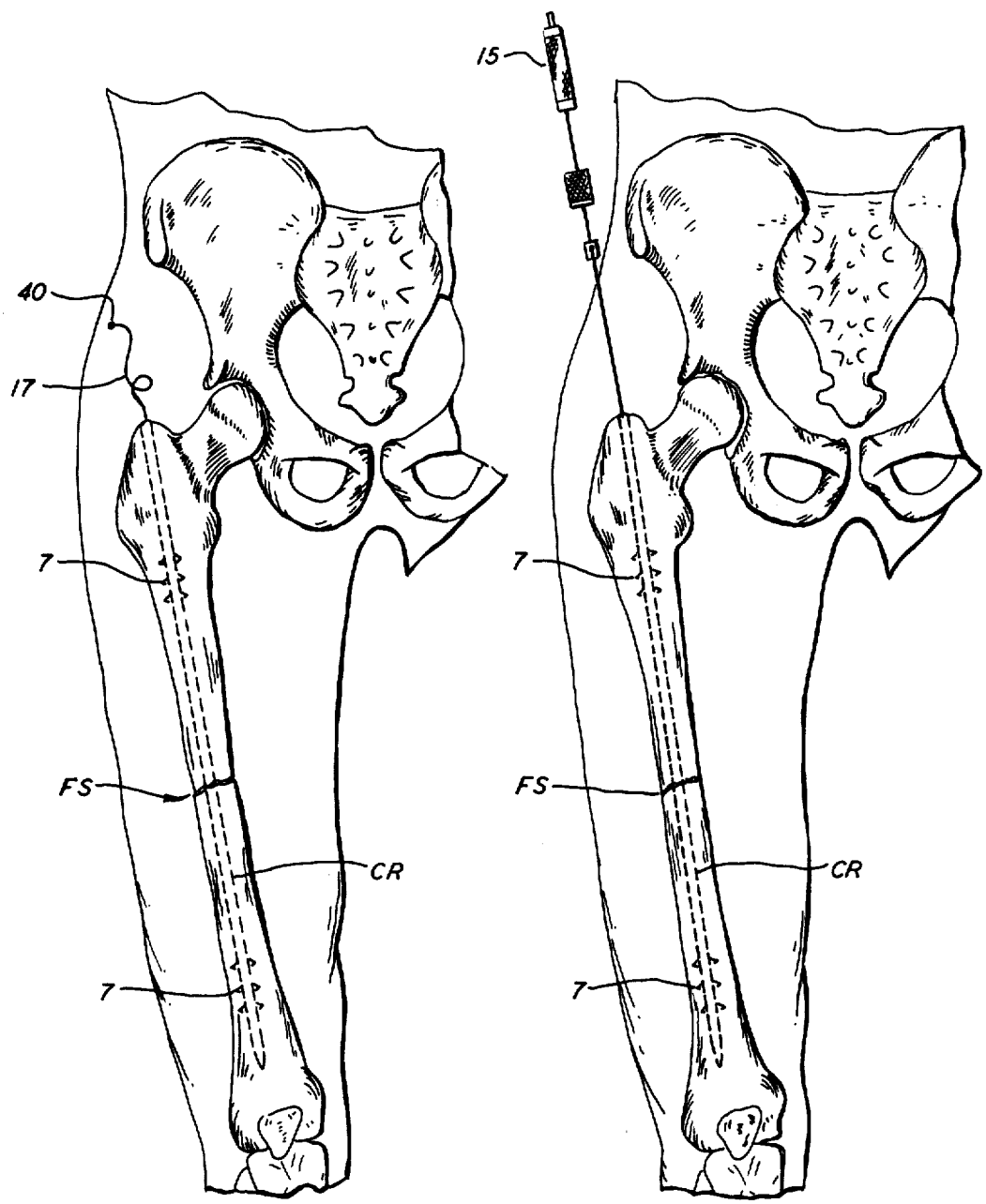
FIG. 9 is an illustration of the nail in place with the extraction cable below the skin and available for removal.
FIG. 10 illustrates one technique of removing the nail.

FIG. 4 illustrates the body 4 of the distal part of the nail. Its relationship to the proximal part shown on FIG. 10 is evident from the overall view of FIG. 1. The central shaft 5 extends therethrough. Within a recess in the body 4 are contained a pair of sliding blades 1 and 2 with lateral projections 7. Suitable opening in the body 4 of the nail permit the radial extension of projections or spikes 7. The axial compression shaft 5 contains pins 8 which engage slots 3 in the sliding blades 1 and 2. At the distal end these slots simply comprise oblique angular slots. On insertion of the nail, the spikes are retracted and the pins 8 will be at the ends of the slots 3 opposite to that shown on the figure. Similar sliding blades with lateral projections 7 are provided at the proximal end as shown on FIG. 3. Again, the pins 8 are present as are slots 3. However, in this instance, the slots 3 contain an angled portion followed by an axial portion extending parallel to the axial compression shaft.

Figures 5, 6:
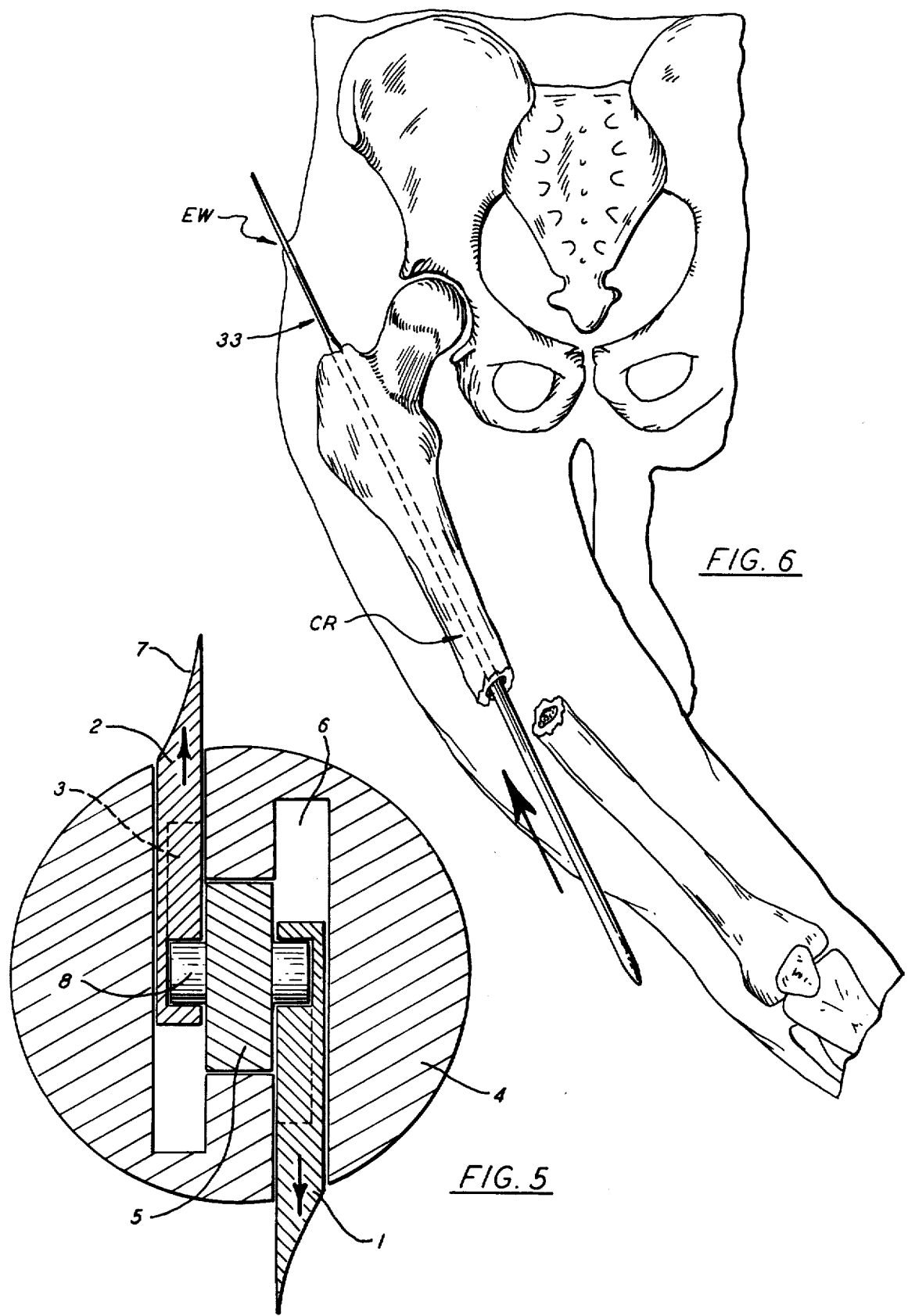
FIG. 5 is a cross-section through the arrangement of FIGS. 3 and 4 illustrating operation of the spikes.
FIG. 6 illustrates the use of the nail in the open nailing technique.

A cross-section of the nail showing the sliding blades 1 and 2 associated with both FIGS. 3 and 4 is shown on FIG. 5. In operation, as the retracting screw head 14 is rotated it draws on the axial compression shaft 5 creating a force F. Because of the spring 27, initially, what will occur is that the shaft 5 will move in the direction of the force F shown on FIG. 4 moving upward in the slots 3, causing the sliding blades with the lateral projections 7 in the distal end to project outward and engage the cortical bone resulting in solid axial and rotational stability as shown in FIG. 2. When the pins 8 of FIG. 8 reach the position shown, further retraction of the shaft will tend to withdraw the distal end 11 of FIG. 1, toward the proximal end 12, against the force of spring 27 creating a compression. In the meantime, at the proximal end the pins 8 were travelling in the slots 3 therein causing the sliding blades with the projection 7 at that end to extend through the openings formed in the proximal part and into the bone. Now, further rotation of the retracting screw head will result a compression of the two bone pieces. As noted above, such is quite important in many instances.

In using the nail of the present invention, open nailing is possible. This is the classical and most generally applicable technique of intramedullary nailing. It includes a retrograde insertion of the nail as shown on FIG. 6. Preoperative skeletal traction is used for 2 to 4 days, until fragments are distracted at least 1 cm. The correct length of the nail is determined radiographically before surgery. The fracture is usually opened through a lateral thigh approach as described by Kuntschner, cited above. The medullary canal CR is reamed from the fracture site. The nail is then driven in the proximal fragment as shown in FIG. 6 and brought out through a secondary skin incision EW over the greater trochanter. The fracture is then reduced and the nail is driven into the distal fragment. When using the open nailing technique, as is evident from FIG. 6, the flexible extraction cable, to be described in more detail below, is covered by a protective sheath 33, as shown in more detail in FIG. 7. The sheath 33 has a sharp tip which facilitates penetration of the proximal end through the muscles and soft tissues of the hip. The sheath is then removed and replaced by a driver inserter 42, shown in more detail on FIG. 8. As illustrated, the driver inserter 42 includes a recess to receive the cable 17 and has a tip 41 which engages the hexagonal opening 19 shown on FIG. 3.

The nail is then driven into the distal bone fragment using the handle hammer 43 shown in FIG. 8. Thereafter, the process of rotating the tool to carry out the extension of the projections 7 is performed in the manner described above.

The use of the protective sheath 33 eliminates the need for a secondary skin incision over the greater trochanter to facilitate the exit of the proximal tip of the nail, since the top sharp tip of the protective sheath will penetrate the tissue with ease as shown in FIG. 6.

It is also possible to carry out closed nailing with the use of a mobile X-ray image intensifier having a television monitor to visualize the reduction of the fracture and the introduction of the guide pins and flexible reamers. under direct X-ray control. This technique has lately gained popularity in the United States because of the disadvantage associated with the open technique where it is necessary to open the fracture site resulting in additional stripping of soft tissue from the bone with further loss of blood supply and greater risk of infection.

It is also possible to carry out semi-closed nailing in which a small skin incision is made over the fracture site the fracture reduced with a bone hook. When using this technique, a guide wire is then inserted into the greater trochanter and driven across the fracture site into the distal fragment. After adequate reaming of the medullary canal with a flexible reamer, the nail is introduced over the guide wire and driven across the fracture site.

After the reduction is carried out, the bone with nail in place will appear as shown on FIG. 9. As illustrated, with the tool removed, the flexible cable 17, which is firmly attached to the proximal end of the nail, is curled and buried under the skin in the subcutaneous tissue. When the fracture is healed and bone continuity restored, the nail can be removed by exposing the tip of the flexible cable which is used as a guide wire to guide the tip 41 of the insertion and extraction tool 42 of FIG. 8, down to the proximal tip of the nail. At this time, the tip becomes lodged in the extraction recess 28 of FIG. 3 and traction can be applied to remove the nail.

It is also possible instead of using the tool of FIG. 8 for extraction, to make a simple skin incision and expose the tip of the flexible cable and apply to the tip 40, shown on FIG. 7b, an extractor 15 of the type shown in FIG. 10, e.g., a McNutt driver extractor, or a McReynolds driver extractor. The tip of the extractor device is attached to the tip 40 of the extractor cable 14 and the nail extracted by striking out the hammer handle. Such a technique is very useful in cases where the proximal tip of the nail is covered by overgrowing bone.

As illustrated by FIG. 7, the tip of the flexible extraction cable 17, preferably contains a thread 34 to permit interchangeable heads. Shown on FIG. 7 is a small head 35 and in FIG. 7a a larger dull, interchangeable head or tip 40. Also shown on FIG. 7, which illustrates the protective sheath is a ball lock 36, which snaps within the recess 28 at the proximal part to hold the sheath in place.

FIG. 11 illustrates the manner of attachment of the flexible cable 17 to the retracting screw head 14, which in turn is connected to the axial shaft 5. As illustrated, cable 17 has a rigid part 30 at its end, which is enlarged and imbedded within the retracting screw head 14 below the hexagonal recess 19.

FIGS. 12, 13 and 14, illustrate in more detail the insertion and retraction head 41 of the tool of FIG. 8. Referring to FIGS. 12 and 8, it can be seen that the inserter driver 42 contains a recess into which the flexible cable 17 is inserted, the flexible cable 17 acting as a guide for the tool. The tip 41 of the insertion and removal tool 42 is connected to a body portion 23 as shown on FIG. 8. At the tip 41, there are provided opposed flanges 25, which extend outwardly therefrom, and, therebelow, a hexagonal tip 22 in the nature of an Allen wrench for insertion and retraction. The tip 41 in place is shown by the views of FIGS. 13 and 14. As shown, the hexagonal portion 22 is fitted into the opening 19 to permit rotation of the retracting screw head 14. At the top of the proximal end of the nail, there is a slotted opening 21 to permit the flanges 25 to pass below a lip 16 formed at the end of the nail. Thereafter, rotation of the tip 41 of the inserter driver will result in the flanges 25 being below the lip 16 to permit retraction.

Thus, when it is desired to retract the nail, after the bone has regenerated, the tip of the tool 41 is inserted as shown on FIGS. 13 and 14, and the retraction and insertion tool 42 rotated to carry out an operation opposite to that described above concerning insertion of the nail. In other words, a rotation is carried out to bring about a force opposite to the force F shown on FIG. 3. This results in the spike 7 being retracted to within the nail. Once this takes place, it is then possible, in the manner described above, to to apply the necessary tension to the hammer handle 43 of FIG. 8 or use the tool of FIG. 10 to withdraw the nail.

The nail of the present invention must be made of non-corrosive materials and all parts must be electrically compatible with each other. Examples of materials which may be used are those conventional in orthopedic devices such as stainless steel, titanium, vitalium, etc.

Further, although the nail is shown with a circular cross-section, it may also have a diamond, square, rectangular, octagonal, etc., cross-section. In addition, although in FIGS. 3 and 4 only two or three spikes 7 are shown on each side of the nail, more may be provided as may more sets of spikes. More important, however, because of differences in the diameter of the medullary canal, the size and or degree of projection of the spikes must be adjusted. In other words, contrary to what is shown in the Figures where all spikes 7 are the same, when making a nail for a specific use the profile of the extending tips should approximate the profile of the medullary canal with which the nail is to be used.

What is claimed is:

1. A dynamic compression nail for intramedullary compression nailing in treating the fractures of long bones comprising:
   (a) a proximal part having at its distal end a central cylindrical recess open on the distal end and a central bore through the remaining portion of the part;
   (b) a distal part having a tip portion and a portion attached thereto for insertion into said cylindrical cavity said distal part also containing a central bore;
   (c) a central axial shaft extending through the bores in said proximal and distal parts;
   (d) a spring surrounding said shaft and acting between the proximal end of said cylindrical recess and said distal part biasing said distal part distally;
   (e) at least one pair of sliding blades having laterally directed pointed projections said blades being constrained to slide substantially radially in each of said proximal and distal parts, means operatively coupling said sliding blades to said shaft by slot means in the blades and pins attached to said shaft, said pins extending into said slot means in such fashion that movement of said shaft proximally will slide said blades, from a first position, relative to said shaft, substantially radially outward to a second position; said sliding blades having substantially no axial movement when sliding radially from said first position to said second position; said pointed projections when in said second position being adapted to and positioned for tractically engaging the osseous tissue and adfixing said proximal and distal parts within the medullary canal.
   (f) means for moving said shaft; and
   (g) the slots in the blades installed in said distal part containing only an oblique portion, and the slots in said proximal protion containing an oblique portion at their distal end followed by an axial portion at their proximal end whereby as said shaft is retracted, the sliding blades in said distal end will be extended, the sliding blades in said proximal end extended and then, with further retraction of said shaft, said distal end will be drawn toward said proximal end permitting compression of distal and proximal bone fragments.

2. A nail according to claim 1 wherein said means for moving comprise a retracting screw head disposed within said proximal part, said screw head having a recess therein for receiving the tip of an insertion and retraction tool, said retracting screw head containing at its distal end a coaxial bore having internal threads, the proximal end of said shaft threaded and screwed into said retracting screw head whereby rotation of said retracting screw head will move said shaft axially toward said proximal part.

3. A nail according to claim 1 and further including a flexible retraction cable securely affixed to the proximal end of said nail for use in removal of said nail.

4. A nail according to claim 3 wherein said cable is attached to said retracting screw head.

5. A nail according to claim 4 wherein said cable contains a portion on the proximal end thereof which is threaded and further including an interchangeable tip screwed onto said threaded portion.

6. A nail according to claim 4 and further including a protective sheath having a pointed end and a recess for retaining said cable, said tip disposed over said cable and including means to cause it to be retained in said proximal part of said nail for ease of insertion of said nail into the proximal bone fragment.

7. Apparatus according to claim 5 wherein said retracting screw head is contained within a recess at the proximal end of said nail and further including a lip at the proximal end of said recess, said lip containing cutouts therein and further including an insertion and retraction tool comprising an elongated tool having a tip, said tip including a distal portion of a shape to match the recess in said retracting screw head and proximal thereof, flanges matched to the openings in said lip whereby said tool can be inserted into said opening in said retracting screw head and used to rotate said screw head to insert or remove said projections on said sliding blades; and said tool, when inserted and rotated engages said flanges beneath said lip and can be used for extraction of said nail; said tool also having a central bore for retaining said cable whereby said cable can be used to guide said tip to said retracting screw head when inserting and removing said nail.

8. A nail according to claim 7 wherein said recess and the tip of said tool have a hexagonal shape.

9. A nail according to claim 1 wherein all parts of said nail are made of non-corrosive electrically compatible metals.

10. A nail according to claim 9 wherein said metal is selected from the group consisting of stainless steel, vitalium and titanium.

11. A nail according to claim 1 wherein the profile of said projections when extended at least approximately follow the profile of the medullary canal with which they are to be used.

12. A dynamic compression nail for intramedullary compression nailing in treating the fractures of long bones comprising:
 (a) a proximal part having at its distal end a central cylindrical recess open on the distal end and a central bore through the remaining portion of the part;
 (b) a distal part having a tip portion and a portion attached thereto for insertion into said cylindrical cavity said distal part also containing a central bore;
 (c) a central axial shaft extending through the bores in said proximal and distal parts;
 (d) a spring surrounding said shaft and acting between the proximal end of said cylindrical recess and said distal part biasing said distal part distally;
 (e) at least one pair of sliding blades having laterally directed pointed projections said blades being constrained to slide substantially radially in each of said proximal and distal parts, means operatively coupling said sliding blades to said shaft by slot means in the blades and pins attached to said shaft, said pins extending into said slot means in such fashion that movement of said shaft proximally will slide said blades, from a first position, relative to said shaft, substantially radially outward to a second position; said sliding blades having substantially no axial movement when sliding radially from said first position to said second position; said pointed projections when in said second position being adapted to and positioned for tractically engaging the osseous tissue and adfixing said proximal and distal parts within the medullary canal; and
 (f) means for moving said shaft.

* * * * *